(12) United States Patent
Varoon

(10) Patent No.: US 8,198,901 B2
(45) Date of Patent: Jun. 12, 2012

(54) METHOD FOR ASSESSMENT OF ELECTROSTATIC PROPERTIES OF FIBERS OR SUBSTRATES

(75) Inventor: Kumar Varoon, Minneapolis, MN (US)

(73) Assignee: The Procter & Gamble Company, Cincinnati, OH (US)

( * ) Notice: Subject to any disclaimer, the term of this patent is extended or adjusted under 35 U.S.C. 154(b) by 528 days.

(21) Appl. No.: 12/363,099

(22) Filed: Jan. 30, 2009

(65) Prior Publication Data

US 2009/0195253 A1    Aug. 6, 2009

Related U.S. Application Data

(60) Provisional application No. 61/063,080, filed on Jan. 31, 2008.

(51) Int. Cl.
*G01R 29/12* (2006.01)
*G01N 27/60* (2006.01)

(52) U.S. Cl. ........................ 324/457; 324/452

(58) Field of Classification Search .............. 324/457, 324/452, 451
See application file for complete search history.

(56) References Cited

U.S. PATENT DOCUMENTS

| | | | | |
|---|---|---|---|---|
| 4,885,543 A | * | 12/1989 | Smith | 324/452 |
| 6,332,234 B1 | | 12/2001 | Graham et al. | |
| 6,923,979 B2 | * | 8/2005 | Fotland et al. | 424/439 |
| 2005/0158366 A1 | * | 7/2005 | Fotland et al. | 424/439 |

FOREIGN PATENT DOCUMENTS

| | | |
|---|---|---|
| EP | 523963 A1 | 1/1993 |
| JP | 62294960 | 12/1987 |

* cited by examiner

*Primary Examiner* — Hoai-An D Nguyen
(74) *Attorney, Agent, or Firm* — Linda M. Sivik; James T. Fondriest

(57) ABSTRACT

Method for assessment of electrostatic properties of fibers or substrates, this method being particularly useful for demonstrating the efficacy of a composition for minimizing the accumulation of particles onto fiber or substrate, and for supporting advertising claims about this efficacy.

39 Claims, 1 Drawing Sheet

METHOD FOR ASSESSMENT OF ELECTROSTATIC PROPERTIES OF FIBERS OR SUBSTRATES

This application claims the benefit of U.S. Provisional Application No. 61/063,080, filed on Jan. 31, 2008.

FIELD OF THE INVENTION

The present invention relates to a method for assessment of electrostatic properties of fibers or substrates. The present invention is particularly useful for demonstrating the efficacy of a composition for minimizing the accumulation of particles onto fiber or substrate. The present invention may be utilized for supporting advertising claims.

BACKGROUND OF THE INVENTION

Fibers, e.g. mammal hairs, may attract particles by electrostatic attraction. The accumulation of particles onto mammal hairs is particularly detrimental in environments, e.g. urban environments, comprising a large amount of suspended particles, such as pollen, dust and/or grime. The accumulation of particles onto mammal hairs may damage them and may also impair their appearance and their shininess. The accumulation of particles onto hair is mainly provoked by the electrostatic properties of hair. Electrostatic electricity can be generated by brushing, combing and/or rubbing the hairs and this effect is even more pronounced in damaged hairs.

Electrostatic properties of fibers may be minimized by treatment with compositions. Particularly, electrostatic properties of mammal hairs may be minimized by treating them with hair care compositions, e.g. a conditioning composition, a styling composition and/or a shampoo.

It may be useful to assess the electrostatic properties of untreated and/or treated fibers, or a substrate, in order to determine their ability to attract particles. It may be also useful to compare the electrostatic properties of treated fibers versus untreated fibers in order to determine the efficacy of the treatment composition for minimizing the accumulation of particles onto fibers. It may be also useful to compare the electrostatic properties of fibers treated with different compositions in order to compare the efficacy of the treatment compositions for minimizing the accumulation of particles onto fibers.

Electrostatic properties of fibers or substrates may be assessed by using complex methods, e.g. by measuring these properties via an electrical measuring device. See, e.g. JP62-294960A. In contrast, there is a need for a method for a simple and accurate assessment of electrostatic properties of one sample of at least one fiber. Particularly, there is a need for a method allowing a direct visualization of the electrostatic properties of fibers. There is also a need for a method for a simple and accurate comparison of electrostatic properties of at least two samples of fibers, e.g. an untreated sample versus a sample treated with a composition. There is also a need for a method for a simple and accurate demonstration of the efficacy of a composition for minimizing the accumulation of particles onto fiber or substrate. Particularly, there is a need for a method for a simple and accurate demonstration of the efficacy of a treatment composition for protecting fibers, e.g. mammal hairs, against pollution and/or for maintaining the freshness and/or the smoothness of mammal hairs.

In addition, there is a need for a method which can be easily understood by the non-skilled person, including the consumer and/or the end user. There is also a need for a method for supporting advertising claims about the efficacy of a treatment composition for minimizing the accumulation of particles onto hair. There is also a need for a method for supporting advertising claims about the efficacy of a treatment composition for protecting fibers, e.g. mammal hairs, against pollution and/or for maintaining the freshness and/or the smoothness of mammal hairs. Finally, there is also a need for a method of marketing a hair care composition, which composition is capable of minimizing the accumulation of particles onto fibers or substrates.

SUMMARY OF THE INVENTION

In a first aspect, the present invention relates to a method for assessment of electrostatic properties of fibers or substrates, comprising the steps of:
(1) providing at least one sample of at least one fiber or substrate;
(2) providing a defined sample of particles, which particles are capable of reacting to electrostatic charges;
(3) placing said sample of particles and said sample of at least one fiber or substrate in a defined environment into a quantified close proximity to each other;
(4) maintaining said close proximity for a defined period of time sufficient for the particles to move towards said sample of at least one fiber or substrate by means of the electrostatic attraction between fiber or substrate and particles;
(5) assessing the quantity of particles adhering to said sample of at least one fiber or substrate; and,
(6) utilizing said assessment to support advertising claims.

In a second aspect, the present invention relates to a method for assessment of electrostatic properties of fibers or substrates, comprising the steps of:
(1) providing one sample of at least one fiber or substrate;
(2) providing a defined sample of particles, which particles are capable of reacting to electrostatic charges;
(3) placing said sample of particles and said sample of at least one fiber or substrate in a defined environment into a quantified close proximity to each other;
(4) maintaining said close proximity for a defined period of time sufficient for the particles to move towards said sample of at least one fiber or substrate by means of the electrostatic attraction between fiber or substrate and particles;
(5) assessing the quantity of particles adhering to said sample of at least one fiber or substrate; and,
(6) providing at least one additional sample of at least one fiber or substrate;
(7) repeating steps 2 to 5 with the or each additional sample;
(8) comparing the assessments of the quantity of particles adhering to each sample to define which sample accumulated more of said defined sample of particles; and,
(9) utilizing said comparative assessments to support advertising claims.

In a preferred embodiment, these methods further comprise the step of treating the or at least one sample of at least one fiber or substrate with a composition, which composition is capable of minimizing the accumulation of particles onto fibers or substrates.

DETAILED DESCRIPTION OF THE INVENTION

Figure 1:
FIG. 1 is a schematic figure of step B of the method according to the present invention.
Figure 2:
FIG. 2 is a schematic figure of step C of the method according to the present invention.
Figure 3:
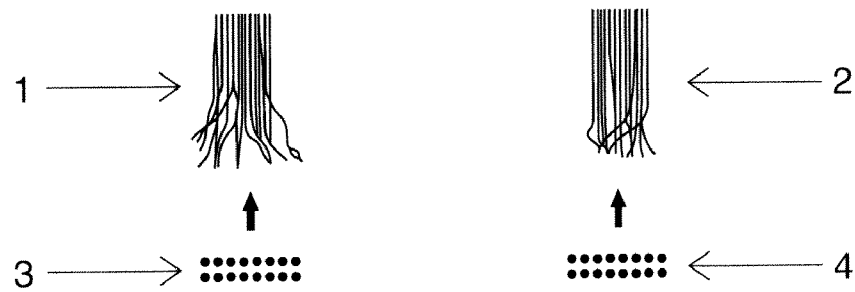
FIG. 3 is a schematic figure of steps D and E of the method according to the present invention.
Figure 4:
FIG. 4 is a schematic figure of step F of the method according to the present invention.
Figure 5:
FIG. 5 is a schematic figure of steps G and H of the method according to the present invention.

The present invention relates to a method for assessment of electrostatic properties of fibers or substrates by assessing the quantity of particles adhering to at least one sample of at least one fiber or substrate. Particularly, the present invention relates to a method for assessing the quantity of particles adhering to at least two samples of at least one fiber or substrate and for defining which sample accumulated more particles. The invention may be useful to demonstrate the efficacy of a sample of at least one fiber or substrate for a minimized accumulation of particles onto it or, in contrast, to demonstrate the efficacy of sample of at least one fiber or substrate for an increased accumulation of particles onto it. The invention may also be useful to demonstrate the efficacy of treatment composition for minimizing the accumulation of particles onto fibers or substrates or, in contrast, to demonstrate the efficacy of treatment composition for increasing the accumulation of particles onto fibers or substrates.

Particularly, when the sample of at least one fiber or substrate is treated with a composition, the present invention also relates to a method for demonstrating the efficacy of a composition for minimizing the accumulation of particles onto fibers or substrates. When at least two samples of at least one fiber or substrate are treated with different compositions, the present invention also relates to a method for comparing the efficacy of different compositions for minimizing the accumulation of particles onto fibers or substrates. The present invention is useful for supporting advertising claims.

The inventors have found that electrostatic properties of fibers, e.g. mammal hair, can be assessed by using a simple and accurate method comprising the steps of providing at least one sample of at least one fiber or substrate and a sample of particles, placing and maintaining them in close proximity to each other. In result, the particles, or at least some of the particles, move towards the or each sample of at least one fiber or substrate and it can be assessed the quantity of particles adhering to the or each sample of at least one fiber or substrate. Without wishing to be bound by any theory, it is believed that the motion of particles towards the or each sample of fiber or substrate is mainly due to electrostatic attraction and that fibers such as mammal hair may carry an electrostatic charge, especially after rubbing, brushing and/or combing, that may attract further particles onto fibers.

The inventors have also found that this method may be used for supporting advertising claims. When the or at least one sample of at least one fiber is treated with a composition, the method is useful for demonstrating the efficacy of a composition for minimizing accumulation of particles onto fibers or substrates. This demonstration may be utilized for supporting advertising claims about the efficacy of this composition for minimizing accumulation of particles onto fibers or substrates and/or for marketing said composition. More generally, the method is useful for demonstrating the efficacy of a composition for protecting hair against pollution and the demonstration may be utilized for supporting advertising claims about the efficacy of this composition for protecting hair against pollution and/or for marketing said composition. Particularly, the inventors have found that this simple and accurate method allows the non-skilled person, i.e. the consumer and/or the end user, to easily assess the efficacy of a composition and to easily compare this efficacy with the efficacy of other compositions and/or with the absence of treatment. Without wishing to be bound by any theory, it is believed that the consumer and/or the end-user, who is usually a non-skilled person, wishes the advertising claims to be proved/supported by experimental results. It is also believed that conducting this method in front of the consumer and/or the end user may convince him/her of the efficacy of the composition and may convince him/her to buy and/or use this composition.

The invention is also useful for demonstrating the efficacy of a substrate (e.g. a substrate having anti-static properties, a substrate for removing and/or attracting dust, a substrate for cleansing hard surfaces, or combinations thereof) for increasing the accumulation of particles onto it. This demonstration may be utilized for supporting advertising claims about the efficacy of this substrate for removing and/or attracting dust and/or for cleansing hard surfaces and/or for marketing this substrate.

The method comprises the provision of at least one sample of at least one fiber or substrate, preferably from one to five samples of at least one fiber and substrate, and more preferably two samples of at least one fiber and substrate.

As used herein, "fiber" means any fiber that is susceptible to carry an electrostatic charge inherently and/or after rubbing, combing and/or brushing. Said fiber is preferably a mammal hair, more preferably a human hair and still more preferably a female human hair. Said mammal hair may be a cut hair. This fiber carries preferably a charge from +1 KV (KiloVolts) to +30 KV, more preferably from +10 KV to +15 KV.

As used herein, "substrate" means any fiber equivalent material. Said substrate is preferably a mammal hair equivalent material, more preferably a human hair equivalent material. For example, human hair equivalent material may be conventional artificial hairs. Alternatively, said substrate may be selected from a substrate useful for cleaning hard surface, a substrate having anti-static properties, a substrate useful for removing and/or attracting dust, or combinations thereof.

The or each sample of at least one fiber may comprise a multitude of fibers which are bundled together at one end. The or each sample is preferably suspended vertically with the free end of said fibers hanging down such that the fiber ends are all in substantially the same horizontal plane (step B).

Said sample is preferably a sample of a strand of mammal hairs. Said sample of hairs have preferably a weight from 0.1 to 10 grams, more preferably from 0.1 grams to 5 grams, still more preferably from 0.1 to 1 gram. Said hairs have also preferably a length from 1 cm to 50 cm, more preferably from 5 cm to 30 cm, and still more preferably from 6 cm to 12 cm. When it is provided at least two samples of hairs, these samples have the same number of individual hairs with a deviation of +/−50%, preferably +/−30%, more preferably +/−10%, hairs between samples.

The method also comprises the provision of a defined sample of particles, which particles are capable of reacting to electrostatic charges (step D). As used herein "defined sample" means a sample which can be reproduced and which may be defined by parameters such as the number of particles, the total weight of particles, the total volume of particles, and/or by any other appropriate parameters known by the skilled person.

Particles, which are suitable for use in the present method, include any conventional particles which are capable of reacting to electrostatic properties. Particles may be organic particles and/or inorganic particles and they may be defined by different parameters, including their specific gravity, particle size, weight, electrical conductivity and charge. Particles have preferably a specific gravity (unitless) from 0.1 to 1, more preferably from 0.4 to 0.7. Preferably, as far as the electrical conductivity is concerned, particles are reactive to electrostatic charge stimulus. Preferably, particles have a charge which is neutral or which is complementary to the fibers or the substrate. Such particles include, for example, white wheat flour particles such as that sold under the trade name Pillsbury Chakki Atta® by General Mills India Pvt. Ltd, and foamed polystyrene particles such as those having a spherical shape and a diameter of from about 0.1 mm to from about 2 mm, preferably from about 0.5 mm to about 1.5 mm.

Particles may also have a different color to the or each sample of at least one fiber or substrate. Particularly, when the assessment of the quantity of particles is determined by visual inspection, it is preferred particles to have a color contrasting with the sample of at least one fiber or substrate. For example, if it is provided dark hairs, e.g. brown or black hair, then it is preferred to provide light-colored particles, e.g. white or beige. Particles may also be capable of being distinguished from fibers or substrates under conditions alternative to daylight conditions, such as in the absence of any light (e.g. fluorescent and/or phosphorescent particles) and/or under infra-red light.

The method also comprises the step of placing the sample of particles and the or each sample of at least one fiber or substrate in a defined environment into a quantified close proximity to each other (step E).

As used herein "a defined environment" means an environment which is controlled and reproducible and which may be defined by parameters such as the relative humidity, the temperature and/or the light conditions. The environment has preferably a relative humidity from 0.1% to 60%, more preferably from 0.1% to 45%. A low relative humidity is preferred as it facilitates generation of electrostatic charge. In contrast, the temperature is not critical when performing the present method. Nevertheless, when wanting to simulate external environment, it may be useful to perform the method at temperatures from −5° C. to 15° C. to reproduce cold winter conditions or at temperatures from 15° C. to 30° C. to reproduce warm summer conditions. The light conditions are not critical either. Nevertheless, when the assessment of the quantity of particles is determined by visual inspection, it is preferred to have light conditions which are sufficient to see the particles and the or each sample of at least one fiber or substrate.

The defined environment is preferably an enclosed chamber of which relative humidity, temperature and/or light conditions can be controlled, more preferably an air-conditioned chamber.

As used herein, "a quantified close proximity" means a distance between the sample of particles and the or each sample of at least one fiber or substrate at which the fibers or substrates may attract the particles by electrostatic charge. The quantified close proximity is preferably from 0 cm to 1 cm, more preferably from 0 cm to 0.5 cm.

Preferably, the or each sample of particle is provided from below the fibers and placed in said quantified close proximity to the end of the fibers. When the particles are provided from below, they may be contained into a containment means so that the upper surface of the sample of particles is substantially horizontal.

The method also comprises the step of maintaining the close proximity between the sample of particles and the or each sample of at least one fiber or substrate for a defined period of time sufficient for the particles to move towards the or each sample of at least one fiber or substrate by means of the electrostatic attraction between fiber or substrate and particles (step F). The period of time is preferably from 5 sec to 2 min, more preferably from 10 sec to 1 min, still more preferably from 20 sec to 40 sec.

The method also comprises the step of assessing the quantity of particles adhering to the or each sample of at least one fiber or substrate (step G).

Preferably, the quantity of particles adhering to the fibers or substrates is assessed by direct visual inspection and/or by picture analysis. Direct visual inspection comprises the step of looking at the or each sample of at least one fiber or substrate, without needing any electrical measuring device. Picture analysis comprises the step of taking pictures of the or each sample of at least one fiber or substrate, optionally treating and/or modifying pictures such as increasing the contrast between the fibers or substrates and the particles, and analyzing the pictures by visual inspection or via a computer-aided inspection.

The direct visual inspection or the picture analysis may be conducted by the skilled person and/or by the non-skilled person, including the consumer and/or the end-user. When the inspection is conducted by a non-skilled person, this person may not need to be trained before the inspection as the assessment of the electrostatic properties of fibers or substrates, derived to the assessment of the quantity of particles adhering to the or each sample of at least one fiber or substrate, is easily understandable.

Alternatively, the quantity of particles adhering to the fibers or substrates may be assessed by measuring the difference between the weight of the or each sample of at least one fiber or substrate before and after placing them in said close proximity to said particles. For example, when this sample comprises a multitude of fibers which are bundled together to one end and this sample is suspended vertically with the free end of said fibers hanging down, this sample may be suspended to a means adapted to measure weight of this sample. Alternatively or complementary to measure the weight of the or each sample of at least one fiber or substrate, the quantity of particles adhering to the fibers or substrates may be assessed by measuring the difference between the weight of the defined sample of particles before and after placing it in said close proximity to the or each sample of at least one fiber or substrate.

When it is provided at least two samples of at least one fiber or substrate, the steps of providing each sample of at least one fiber or substrate, providing a sample of particles, placing said sample of particles and each sample of at least one fiber or substrate into close proximity to each other, maintaining said close proximity and then assessing the quantity of particles adhering to each sample of at least one fiber or substrate are conducted in substantially identical conditions. Preferably, all same steps, e.g. placing the sample of particles and the samples of at least one fiber or substrate into close proximity to each other, are conducted simultaneously for all samples, and, more preferably, the samples of at least one fiber or substrate are placed side-by-side.

As used herein, "substantially identical conditions" means a substantially identical defined sample of particles, a substantially identical defined environment, a substantially identical quantified close proximity and a substantially identical defined period of time.

When the methods for assessment of electrostatic properties of at least two samples of at least one fiber or substrate are conducted in substantially identical conditions, the assessments of the quantity of particles adhering to each sample of at least one fiber or substrate may be compared to define which sample accumulated more of said sample of particles (step H).

The method also comprises the step of utilizing the assessment and/or the comparative assessment to support advertising claims (step I). This is particularly advantageous when the method is displayed to the non-skilled person, preferably the consumer and/or the end-user, as this method may be displayed in association with advertising claims.

When the sample of at least one fiber or substrate is treated with a composition capable of minimizing the accumulation of particles onto fibers or substrates, the method comprises the step of utilizing the assessment of the quantity of particles adhering to the sample of at least one fiber or substrate to support advertising claims about the efficacy of said composition for minimizing the accumulation of particles onto fibers or substrates.

Preferably, when the or at least one sample of mammal hairs is treated with a hair care composition, the method comprises the step of utilizing the assessment of the quantity of particles adhering to the sample of mammal hairs to support advertising claims about the efficacy of said composition for minimizing the accumulation of particles, e.g. pollen, dust and/or grime, onto the mammal hairs, and preferably to support advertising claims about the efficacy of said composition for protecting hair against pollution and/or for maintaining the freshness and/or the smoothness of hairs.

Alternatively, when the substrate is selected from a substrate useful for cleansing hard surface, a substrate having anti-static properties, a substrate useful for removing and/or attracting dust, or combinations thereof, the method comprises the step of utilizing the assessment of the quantity of particles adhering to the sample of this substrate to support advertising claims about the efficacy of said substrate for increasing accumulation of particles, and preferably for removing and/or attracting dust and/or cleansing hard surfaces.

Preferably, the method is recorded and incorporated, in combination with the advertising claims, into a commercial, which commercial is capable to be displayed onto any image diffusion support, e.g. television screens, computer screen, theatre screen, in-store screen accessible to the consumer and/or the end user.

When the method is recorded, it may not be necessary to record the step of treating the, at least one or each sample of at least one fiber or substrate with a composition. Instead, it may be recorded the step of indicating that the, at least one or each sample of at least one fiber or substrate has been treated previously with a composition.

Optionally, the method may also comprise the step of treating the, at least one or each sample of at least one fiber or substrate with a composition, which composition is capable of minimizing the accumulation of particles onto fibers or substrates (step A). Without wishing to be bound by any theory, it is believed that the minimization of the accumulation of particles onto fibers or substrates is mainly due to the minimization of the electrostatic properties of fibers or substrate. Preferably, this step is conducted after providing this sample of at least one fiber or substrate but before providing a defined sample of particles.

When it is provided a sample of mammal hairs or a hair equivalent material, any conventional hair care composition suitable for minimizing the electrostatic properties of fibers or substrate may be used. This hair care composition may be a conditioning composition, a styling composition and/or a shampoo. As used herein, "conditioning composition" means a composition comprising at least one conditioning active agent. The conditioning active agent may be selected from any conventional conditioning agent, including some silicone components, some fatty alcohol, etc. Suitable examples of hair conditioning agents may be found in the CTFA International Cosmetic Ingredient Dictionary and Handbook, 11$^{th}$ edition, 2006.

When it is provided at least two samples of at least one fiber or substrate, these samples may be treated by different compositions, or at least one sample may be untreated while the or each other sample is treated by a composition. Preferably, it is provided two samples of mammal hairs, the first sample being not treated and the second sample being treated with a hair care composition capable of minimizing the accumulation of particles onto fibers or substrate, e.g. a hair conditioning composition. It is advantageous to provide at least two samples of at least one fiber or substrate having received different treatments in order to assess the quantities of particles adhering to the samples and to compare these assessments to define which sample accumulated more particles and, consequently, to demonstrate the efficacy of a composition for minimizing the accumulation of particles onto fibers or substrates.

In addition to the step of treating the, at least one or each sample of at least one fiber or substrate with a composition, it may be needed to conduct the step of indicating, by any appropriate manner, that this sample has been treated with the composition. Particularly, this further step may be useful when the, at least one or each sample of at least one fiber or substrate with a composition is treated at least 30 minutes, preferably at least 1 hour, more preferably at least 12 hours, before placing the sample of particles and the or each sample of at least one fiber or substrate into close proximity to each other.

Alternatively, the method may also comprise the step of treating the, or at least one or each sample of at least one fiber or substrate with a composition, which composition is capable of increasing the accumulation of particles onto fibers or substrates. When it is provided a substrate selected from a substrate useful for cleaning hard surface, a substrate having anti-static properties, a substrate useful for removing and/or attracting dust, or combinations thereof, any conventional composition suitable for increasing the accumulation of particles onto substrates may be used.

Optionally, the method may also comprise the step of treating the or each sample of at least one fiber or substrate with methods enhancing the electrostatic charge of fibers or substrate within 10 minutes, preferably within 3 minutes, more preferably within 1 minute (step C). Preferably, these methods enhancing the electrostatic charge are selected from brushing, combing and/or rubbing the fiber or fibers. Preferably, this step is conducted before placing the sample of particles in close proximity to the or each sample of particles. When the, at least one or each sample is treated with a composition, this step is conducted after treatment of the, at least one or each sample. It is advantageous to brush, comb and/or rub hairs as it would enhance the electrostatic charge of hairs and, consequently, it would increase the motion of particles towards the or each sample of at least one fiber or substrate.

The or each sample may be rubbed with a means enhancing the electrostatic charge of hairs, e.g. a latex glove. Preferably, hairs are rubbed one time from one end to the other end with a latex glove, more preferably by grasping hairs with this latex glove.

A preferred embodiment of the present invention is a method for demonstration of the efficacy of a hair care composition for minimizing the accumulation of particles, e.g. pollen, dust and/or and grime, onto mammal hairs, comprising the steps of:

(1) providing a first sample (1) and a second sample (2) of mammal hairs;
(2) treating the second sample (2) with a hair care composition, which composition is capable of minimizing the accumulation of particles onto mammal hairs (step A),
(3) placing said first and second samples of mammal hairs side-by-side (step B);
(4) treating said first and second samples of mammal hairs with a method enhancing the electrostatic charge of hairs (step C);
(5) providing a defined sample of particles (3, 4), which particles are capable of reacting to electrostatic charges (step D);
(6) placing said sample of particles and said samples of mammal hairs in a defined environment into a quantified close proximity to each other (step E);
(7) maintaining said close proximity for a defined period of time sufficient for the particles to move towards said samples of mammal hairs by means of the electrostatic attraction between mammal hairs and particles (step F);
(8) assessing the quantity of particles adhering to each sample of mammal hairs (step G);
(9) comparing the assessments of the quantity of particles adhering to each sample to define which sample accumulated more particles (step H); and,
(10) utilizing said comparison to support advertising claims about the efficacy of said hair care composition for minimizing the accumulation of particles and/or for maintaining the freshness and smoothness of mammal hairs (step I).

Another preferred embodiment of the present invention is a method of marketing a hair care composition, which composition is capable of minimizing the accumulation of particles onto fibers or substrates, comprising the steps of:

(1) offering for sale said hair care composition;
(2) advertising the efficacy of said hair care composition for minimizing the accumulation of particles and/or for maintaining the freshness and smoothness of mammal hair (step I); and,
(3) demonstrating said efficacy by conducting a method comprising the steps of:
  (a) providing a first sample and a second sample of mammal hairs;
  (b) treating the second sample with a hair care composition, which composition is capable of minimizing the accumulation of particles onto mammal hairs (step A);
  (c) placing said first and second samples of mammal hairs side-by-side (step B);
  (d) treating said first and second samples of mammal hairs with a method enhancing the electrostatic charge of hairs (step C);
  (e) providing a defined sample of particles (3,4), which particles are capable of reacting to electrostatic charges (step D);
  (f) placing said sample of particles and said samples of mammal hairs in a defined environment into a quantified close proximity to each other (step E);
  (g) maintaining said close proximity for a defined period of time sufficient for the particles to move towards said samples of mammal hairs by means of the electrostatic attraction between mammal hairs and particles (step F);
  (h) assessing the quantity of particles adhering to each sample of mammal hairs (step G); and,
  (i) comparing the assessments of the quantity of particles adhering to each sample to define which sample accumulated more particles (step H).

Example

The following example further describes and demonstrates the preferred embodiments within the scope of the present invention. This example is given solely for the purpose of illustration, and is not to be construed as limitations of the present invention since many variations thereof are possible without departing from its scope.

A first sample (1) and a second sample (2) of virgin brown oriental female human hairs are provided. Each sample is a strand of hairs having a weight of about 1 g (total weight) and a length of about 8 cm. The experiment is conducted in an air-conditioned chamber where the temperature ranges from 21° C. to 25° C. and the relative humidity from 40% to 45%.

Step A—The first sample (1) is treated with the non-conditioning shampoo Pantene® Clarifying Shampoo before being dried and brushed. This first sample is the untreated sample, i.e. the sample not treated with a conditioning composition. This sample is wetted with water having a temperature of about 100° F. for about 15 sec. Then, 1 mg of Pantene® Clarifying Shampoo is applied evenly onto this sample by massaging this sample between thumb and forefinger for 30 sec. This sample is then rinsed-off by using water having a temperature of about 100° F. for about 30 sec. The steps of wetting the sample, applying the composition and rinsing-off the sample are repeated a second time. The water in excess is squeezed out and this sample is let become dried for 24 h in the air-conditioned chamber. This sample is combed by using fingers just before conducting step B.

In contrast, the second sample (2) is treated with a conditioning system comprising two compositions, i.e. Rejoice Daily Care System comprising Rejoice® Family Care Shampoo and Rejoice® Family Care conditioner, before being dried and brushed. This second sample is the treated sample. This system is useful for minimizing the accumulation of particles onto hairs. Particularly, Rejoice® Family Care Shampoo comprises dimethicone, cetyl alcohol, guar hydroxypropyltrimonium chloride, hydrogenated polydecene and trimethylolpropane tricaprylate/tricaprate as conditioning agents and Rejoice® Family Care conditioner comprises cyclopentasiloxane, dimethicone, stearyl alcohol and cetyl alcohol as conditioning agents.

This second sample is wetted with water having a temperature of about 100° F. for about 15 sec. Then, 1 mg of Rejoice® Family Care Shampoo is applied evenly onto this sample by massaging this sample between thumb and forefinger for 30 sec. This sample is then rinsed-off by using water having a temperature of about 100° F. for about 30 sec. The steps of wetting the sample, applying the composition and rinsing-off the sample are repeated a second time. The water in excess is squeezed out. Then, 1 mg of Rejoice® Family Care conditioner is applied evenly onto this sample by massaging this sample between thumb and forefinger for 30 sec. This sample is then rinsed-off by using water having a temperature of about 100° F. for about 30 sec. The water in excess is squeezed out and this first sample is let become dried for 24 h in the air-conditioned chamber. This sample is combed by using fingers just before conducting step B.

Step B—Each sample is suspended vertically with the free end of hairs hanging down such that the hair ends are all substantially the same horizontal plane. Both samples are placed side-by-side to each other with the hair ends being substantially in the same horizontal plane and at a distance of about 5 cm to 10 cm to each other. Both samples have substantially the same number of individual hairs.

Step C—Then, both samples are rubbed once from the top end to the bottom end (hair ends) by grasping each sample with a latex glove in order to enhance the electrostatic charge of the hairs.

Step D—Then, it is provided about 10 mg of a sample of white wheat flour particles (3, 4) sold under the trade name Pillsbury Chakki Atta® by General Mills India Pvt. Ltd. These particles are distributed onto a plate so that the upper surface of the sample of particles is substantially horizontal.

Step E—Then, the sample of wheat flour (3, 4) is provided from below the first sample (1) and the second sample (2) and placed in close proximity to the ends of the mammal hair, i.e. from 0 cm to 0.5 cm.

Step F—Then, the sample of particles (3, 4) is maintained in said close proximity, respectively, to the first sample (1) and the second sample (2) for a period of time of about 30 seconds. This period of time is sufficient for the wheat flour particles to move towards the first sample (1) or the second sample (2) of hairs by electrostatic attraction between the hairs and the wheat flour particles. After 30 seconds, the first sample (1) has accumulated more wheat flour particles than the second sample (2).

Steps B to E of the demonstration are recorded and the video obtained is incorporated into a commercial.

Over the 30 second exposure to wheat flour particles, it is superimposed the expressions "non-conditioning shampoo" and "Rejoice Daily Care System" respectively onto the first sample and the second sample in order to indicate which sample has been treated with the composition minimizing the accumulation of particles onto hairs.

This video is displayed onto any image diffusion support and accessible to the skilled person and/or the non-skilled person, e.g. the consumer and/or the end user. Particularly, when is video is intended to be used for commercial purpose, then it is incorporated into a commercial and displayed onto any image diffusion support accessible to the consumer and/or the end user, e.g. television screens, computer screen, theatre screen, in-store screen.

Steps G and H—Then, the skilled person and/or the non-skilled person can assess and compare the quantity of particles adhering to the first sample and the second sample by a mere visual inspection, i.e. by watching the commercial displayed onto screens. The non-skilled person can easily notice that there is significant higher quantity of wheat flour particles accumulated on the hairs of the first sample (non-conditioning shampoo) and, compare to the second sample (Rejoice Daily Care System).

Step I—The commercial also comprises advertising claims in relation to the comparative results obtained and highlighting the long-lasting freshness and smoothness of hairs when using the Rejoice® Daily Care System and the minimization and/or prevention of the particles accumulation, pollen, dust, grime and/or dirty particles, onto hairs. The commercial also displays the Rejoice® Daily Care products to help the consumer and/or the end user to recognize the product.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for assessment of electrostatic properties of fibers or substrates, comprising the steps of:
   (1) providing at least one sample of at least one fiber or substrate;
   (2) providing a defined sample of particles, which particles are capable of reacting to electrostatic charges;
   (3) placing said sample of particles and said sample of at least one fiber or substrate in a defined environment into a quantified close proximity to each other;
   (4) maintaining said close proximity for a defined period of time sufficient for the particles to move towards said sample of at least one fiber or substrate by means of the electrostatic attraction between fiber or substrate and particles;
   (5) assessing the quantity of particles adhering to said sample of at least one fiber or substrate without an electrical measuring device; and,
   (6) utilizing said assessment to support advertising claims.

2. A method, according claim 1, wherein the sample of at least one fiber comprises a multitude of fibers which are bundled together at one end and the or each sample of fibers is suspended vertically with the free end of said fibers hanging down such that the fiber ends are all in substantially the same horizontal plane.

3. A method, according to claim 1, wherein the sample of particles is provided from below the fibers and placed in said quantified close proximity to the ends of said fibers.

4. A method, according to claim 1, wherein the sample of at least one fiber is a sample of a strand of mammal hair having a weight from 0.1 to 1 gram, and a length from 6 cm to 12 cm.

5. A method, according to claim 1, comprising the step of treating the sample of at least one fiber or substrate with a composition, which composition is capable of minimizing the accumulation of particles onto fibers or substrates.

6. A method, according to claim 1, comprising the step of treating the sample of at least one fiber or substrate by methods enhancing the electrostatic charge selected from brushing, combing and/or rubbing the fiber or fibers, within 1 minute, before placing said sample of particles in close proximity to the or each sample of at least one fiber.

7. A method, according to claim 1, wherein the quantity of particles adhering to the fiber or fibers is assessed by direct visual inspection or by picture analysis.

8. A method, according to claim 1, wherein the particles have a different color to the sample of at least one fiber or substrate.

9. A method, according to claim 1, wherein said method is recorded and displayed into a commercial, which is capable to be displayed onto any image diffusion means.

10. A method for assessment of electrostatic properties of fibers or substrates, comprising the steps of:
   (1) providing one sample of at least one fiber or substrate;
   (2) providing a defined sample of particles, which particles are capable of reacting to electrostatic charges;
   (3) placing said sample of particles and said sample of at least one fiber or substrate in a defined environment into a quantified close proximity to each other;
   (4) maintaining said close proximity for a defined period of time sufficient for the particles to move towards said sample of at least one fiber or substrate by means of the electrostatic attraction between fiber or substrate and particles;
   (5) assessing the quantity of particles adhering to said sample of at least one fiber or substrate without an electrical measuring device; and,
   (6) providing at least one additional sample of at least one fiber or substrate;
   (7) repeating steps 2 to 5 with the or each additional sample;
   (8) comparing the assessments of the quantity of particles adhering to each sample to define which sample accumulated more of said defined sample of particles; and,
   (9) utilizing said comparative assessments to support advertising claims.

11. A method, according to claim 10, wherein each sample of at least one fiber comprises a multitude of fibers which are bundled together at one end and each sample of fibers is suspended vertically with the free end of said fibers hanging down such that the fiber ends are all in substantially the same horizontal plane.

12. A method, according to claim 10, wherein each sample of particles is provided from below the fibers and placed in said quantified close proximity to the ends of said fibers.

13. A method, according to claim 10, wherein each sample of at least one fiber is a sample of a strand of mammal hair having a weight from 0.1 to 1 gram, and a length from 6 cm to 12 cm.

14. A method, according to claim 10, wherein said samples have the same number of individual hairs with a deviation of +/−10% hairs between samples.

15. A method, according to claim 10, comprising the step of treating at least one sample of at least one fiber or substrate with a composition, which composition is capable of minimizing the accumulation of particles onto fibers or substrates.

16. A method, according to claim 10, comprising the step of treating each sample of at least one fiber or substrate by methods enhancing the electrostatic charge selected from brushing, combing and/or rubbing the fiber or fibers, within 1 minute, before placing said sample of particles in close proximity to the or each sample of at least one fiber.

17. A method, according to claim 10, wherein the quantity of particles adhering to the fiber or fibers is assessed by direct visual inspection or by picture analysis.

18. A method, according to claim 10, wherein the particles have a different color to the or each sample of at least one fiber or substrate.

19. A method, according to claim 10, wherein said method is recorded and displayed into a commercial, which is capable to be displayed onto any image diffusion means.

20. A method for demonstration of the efficacy of a hair care composition for minimizing the accumulation of particles onto mammal hairs, comprising the steps of:
   (1) providing a first sample and a second sample of mammal hairs;
   (2) treating the second sample with a hair care composition, which composition is capable of minimizing the accumulation of particles onto mammal hairs,
   (3) placing said first and second samples of mammal hairs side-by-side;
   (4) treating said first and second samples of mammal hairs with a method enhancing the electrostatic charge of hairs;
   (5) providing a defined sample of particles, which particles are capable of reacting to electrostatic charges;
   (6) placing said sample of particles and said samples of mammal hairs in a defined environment into a quantified close proximity to each other;
   (7) maintaining said close proximity for a defined period of time sufficient for the particles to move towards said samples of mammal hairs by means of the electrostatic attraction between mammal hairs and particles;
   (8) assessing the quantity of particles adhering to each sample of mammal hairs without an electrical measuring device; and,
   (9) comparing the assessments of the quantity of particles adhering to each sample to define which sample accumulated more particles; and,
   (10) utilizing said comparison to support advertising claims about the efficacy of said hair care composition for minimizing the accumulation of particles and/or for maintaining the freshness and smoothness of mammal hairs.

21. A method of marketing a hair care composition, which composition is capable of minimizing the accumulation of particles onto fibers or substrates, comprising the steps of:
   (1) offering for sale said hair care composition;
   (2) advertising the efficacy of said hair care composition for minimizing the accumulation of particles and/or for maintaining the freshness and smoothness of mammal hair; and,
   (3) demonstrating said efficacy by conducting a method comprising the steps of:
      (a) providing a first sample and a second sample of mammal hairs;
      (b) treating the second sample with a hair care composition, which composition is capable of minimizing the accumulation of particles onto mammal hairs,
      (c) placing said first and second samples of mammal hairs side-by-side;
      (d) treating said first and second samples of mammal hairs with a method enhancing the electrostatic charge of hairs;
      (e) providing a defined sample of particles, which particles are capable of reacting to electrostatic charges;
      (f) placing said sample of particles and said samples of mammal hairs in a defined environment into a quantified close proximity to each other;
      (g) maintaining said close proximity for a defined period of time sufficient for the particles to move towards said samples of mammal hairs by means of the electrostatic attraction between mammal hairs and particles;
      (h) assessing the quantity of particles adhering to each sample of mammal hairs without an electrical measuring device; and,
      (i) comparing the assessments of the quantity of particles adhering to each sample to define which sample accumulated more particles.

22. A method for assessment of electrostatic properties of fibers or substrates, comprising the steps of:
(1) providing at least one sample of at least one fiber or substrate;
(2) providing a defined sample of particles, which particles are capable of reacting to electrostatic charges;
(3) placing said sample of particles and said sample of at least one fiber or substrate in a defined environment into a quantified close proximity to each other;
(4) maintaining said close proximity for a defined period of time sufficient for the particles to move towards said sample of at least one fiber or substrate by means of the electrostatic attraction between fiber or substrate and particles; and,
(5) assessing the quantity of particles adhering to said sample of at least one fiber or substrate without an electrical measuring device.

23. A method, according claim 22, wherein the sample of at least one fiber comprises a multitude of fibers which are bundled together at one end and the or each sample of fibers is suspended vertically with the free end of said fibers hanging down such that the fiber ends are all in substantially the same horizontal plane.

24. A method, according to claim 22, wherein the sample of particles is provided from below the fibers and placed in said quantified close proximity to the ends of said fibers.

25. A method, according to claim 22, wherein the sample of at least one fiber is a sample of a strand of mammal hair having a weight from 0.1 to 1 gram, and a length from 6 cm to 12 cm.

26. A method, according to claim 22, comprising the step of treating the sample of at least one fiber or substrate with a composition, which composition is capable of minimizing the accumulation of particles onto fibers or substrates.

27. A method, according to claim 22, comprising the step of treating the sample of at least one fiber or substrate by methods enhancing the electrostatic charge selected from brushing, combing and/or rubbing the fiber or fibers, within 1 minute, before placing said sample of particles in close proximity to the or each sample of at least one fiber.

28. A method, according to claim 22, wherein the quantity of particles adhering to the fiber or fibers is assessed by direct visual inspection or by picture analysis.

29. A method, according to claim 22, wherein the particles have a different color to the sample of at least one fiber or substrate.

30. A method for assessment of electrostatic properties of fibers or substrates, comprising the steps of:
(1) providing one sample of at least one fiber or substrate;
(2) providing a defined sample of particles, which particles are capable of reacting to electrostatic charges;
(3) placing said sample of particles and said sample of at least one fiber or substrate in a defined environment into a quantified close proximity to each other;
(4) maintaining said close proximity for a defined period of time sufficient for the particles to move towards said sample of at least one fiber or substrate by means of the electrostatic attraction between fiber or substrate and particles;
(5) assessing the quantity of particles adhering to said sample of at least one fiber or substrate without an electrical measuring device; and,
(6) providing at least one additional sample of at least one fiber or substrate;
(8) repeating steps 2 to 5 with the or each additional sample; and,
(9) comparing the assessments of the quantity of particles adhering to each sample to define which sample accumulated more of said defined sample of particles.

31. A method, according to claim 30, wherein each sample of at least one fiber comprises a multitude of fibers which are bundled together at one end and each sample of fibers is suspended vertically with the free end of said fibers hanging down such that the fiber ends are all in substantially the same horizontal plane.

32. A method, according to claim 30, wherein each sample of particles is provided from below the fibers and placed in said quantified close proximity to the ends of said fibers.

33. A method, according to claim 30, wherein each sample of at least one fiber is a sample of a strand of mammal hair having a weight from 0.1 to 1 gram, and a length from 6 cm to 12 cm.

34. A method, according to claim 30, wherein said samples have the same number of individual hairs with a deviation of +/− 10% hairs between samples.

35. A method, according to claim 30, comprising the step of treating at least one sample of at least one fiber or substrate with a composition, which composition is capable of minimizing the accumulation of particles onto fibers or substrates.

36. A method, according to claim 30, comprising the step of treating each sample of at least one fiber or substrate by methods enhancing the electrostatic charge selected from brushing, combing and/or rubbing the fiber or fibers, within 1 minute, before placing said sample of particles in close proximity to the or each sample of at least one fiber.

37. A method, according to claim 30, wherein the quantity of particles adhering to the fiber or fibers is assessed by direct visual inspection or by picture analysis.

38. A method, according to claim 30, wherein the particles have a different color to the or each sample of at least one fiber or substrate.

39. A method for demonstration of the efficacy of a hair care composition for minimizing the accumulation of particles onto mammal hairs, comprising the steps of:
(1) providing a first sample and a second sample of mammal hairs;
(2) treating the second sample with a hair care composition, which composition is capable of minimizing the accumulation of particles onto mammal hairs,
(3) placing said first and second samples of mammal hairs side-by-side;
(4) treating said first and second samples of mammal hairs with a method enhancing the electrostatic charge of hairs;
(5) providing a defined sample of particles, which particles are capable of reacting to electrostatic charges;
(6) placing said sample of particles and said samples of mammal hairs in a defined environment into a quantified close proximity to each other;
(7) maintaining said close proximity for a defined period of time sufficient for the particles to move towards said samples of mammal hairs by means of the electrostatic attraction between mammal hairs and particles;
(8) assessing the quantity of particles adhering to each sample of mammal hairs without an electrical measuring device; and,
(9) comparing the assessments of the quantity of particles adhering to each sample to define which sample accumulated more particles.

* * * * *